United States Patent [19]

Pan et al.

[11] Patent Number: 4,588,829

[45] Date of Patent: May 13, 1986

[54] (DISULFIDO)TRIS(N,N-SUBSTITUTED DITHIOCARBAMATO)MO(V) COMPLEXES

[75] Inventors: Wie-Hin Pan, Columbia, Md.; Edward I. Stiefel, Bridgewater, N.J.

[73] Assignee: Exxon Research & Engineering Company, Florham Park, N.J.

[21] Appl. No.: 635,283

[22] Filed: Jul. 27, 1984

[51] Int. Cl.[4] .............................................. C07F 11/00
[52] U.S. Cl. ..................................................... 556/38
[58] Field of Search ...................... 260/429 K; 556/38

[56] References Cited

U.S. PATENT DOCUMENTS 3,706,819  12/1972  Usamoto et al. ........... 260/429 K X
4,098,705  7/1978   Sakurai et al. ............. 260/429 K X

FOREIGN PATENT DOCUMENTS 2635511   2/1977  Fed. Rep. of Germany ... 260/429 K
48-48448  12/1974 Japan .............................. 260/429 K
51-80825  7/1976  Japan .............................. 260/429 K

OTHER PUBLICATIONS

Chemical Abstracts 85 201421s, (1976).
Chemical Abstracts 86 83036r, (1977).
Chemical Abstracts 89 139639w, (1978).
Chemical Abstracts 94 129874h, (1981).
Chemical Abstracts 89 69916h, (1978).
Chemical Abstracts 87 126465v, (1977).
Chemical Abstracts 92 157026k, (1980).
Chemical Abstracts 91 203504u, (1979).

Primary Examiner—Helen M. S. Sneed
Attorney, Agent, or Firm—Edward M. Corcoran

[57] ABSTRACT

This invention relates to (disulfido)tris(N,N-substituted dithiocarbamato)Mo(V) complexes. More particularly, this invention relates to compounds of the formula $MoS_2(S_2CNR_2)_3$ which are mononuclear, eight-coordinate, neutral Mo(V) complexes containing only eight sulfur atoms in the Mo coordination sphere. R is hydrogen, an alkyl, aryl, cycloalkyl group or mixture thereof. Preferably all of the R's are the same and are alkyl groups. These compounds are useful as lubricant additives.

12 Claims, No Drawings

(DISULFIDO)TRIS(N,N-SUBSTITUTED DITHIOCARBAMATO)Mo(V) COMPLEXES

BACKGROUND OF THE INVENTION

1. Field of the Invention

This invention relates to (disulfido)tris(N,N-substituted dithiocarbamate)Mo(V) complexes. More particularly, this invention relates to compounds of the formula $MoS_2(S_2CNR_2)_3$ which are mononuclear, eight-coordinate, neutral Mo(V) complexes containing only eight sulfur atoms in the Mo coordination sphere.

2. Background of the Disclosure

Molybdenum and sulfur each display redox activity which profoundly influences their chemistry. $MoS_4^{2-}$ and organic disulfides react by a process involving induced internal electron transfer to yield the binary anion $[Mo_2(\mu-S)_2(S)_2(S_2)_2]^{2-}$. This anion is formally the dimer of the one-electron oxidation product of $MoS_4^{2-}$ and no atoms are added or removed. The addition of an oxidant RSSR to the hexavalent $MoS_4^{2-}$ leads to a reduced product, i.e., the dinuclear Mo(V) complex in a reaction involving an induced internal electron transfer.

Miller et al in "$Mo_2S_4^{2+}$ Core: New Syntheses, New Complexes, and Electrochemical Diversity", *J.A.C.S.*, 102, 5102 (1980) reported dinuclear molybdenum compounds containing both sulfide ($S^{2-}$) ligands and diethyl dithiocarbamates. A. Nieuwpoort in "New Compounds Containing Molybdenum and Diethyldithiocarbamate", *J. Less Common Metals*, 36, 271 (1974) disclosed non-neutral, eight-coordinate, N,N-diethyldithiocarbamate Mo(V) cation complexes which do not contain a disulfide ligand in the Mo coordination sphere. Dirand et al, "The Reaction of $MoO_2(S_2CNPr_2)_2$ and $H_2S$: Preparation and Molecular Structure of a New Disulfur Complex: $MoO(S_2)(S_2CNPr_2)_2$", *Inorg. Nucl. Chem. Lett.*, 11, 661-4 (1975), disclosed a Mo(VI) complex which contains an oxo ligand in addition to two N,N-dipropyldithiocarbamato groups and a disulfide ligand. However, no previously disclosed compound contains both $S_2^{2-}$ and dithiocarbamate ligands in a Mo(V) coordination sphere with eight sulfur atoms bound to the Mo.

SUMMARY OF THE INVENTION (Disulfido)tris(N,N-substituted dithiocarbamato)-Mo(V) complexes have now been prepared. These are new compositions of matter which are mononuclear, eight-coordinate neutral, Mo(V) complexes containing only eight sulfur atoms in the Mo coordination sphere and have the general formula $MoS_2(S_2CNR_2)_3$ wherein R is H, an alkyl group, cycloalkyl group, aryl group or mixture thereof and preferably an alkyl group. These new compositions have the following structure:

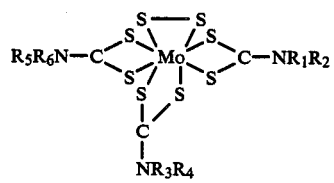

wherein $R_1$, $R_2$, $R_3$, $R_4$, $R_5$ and $R_6$ are the same or different and are H, an alkyl group, aryl group and cycloalkyl group. Preferably $R_1$, $R_2$, $R_3$, $R_4$, $R_5$ and $R_6$ are the same and will be an alkyl group.

These new compounds have been found to be useful lubricant additives and have been prepared by reacting a substituted ammonium tetrathiomolybdate with a thiuramdisulfide in non-aqueous media under an inert atmosphere.

DETAILED DESCRIPTION (Disulfido)tris(N,N-substituted dithiocarbamato)-Mo(V) complex compounds of the formula $MoS_2(S_2CNR_2)_3$ and of the structure set forth above have now been prepared. These new compounds are mononuclear, eight-coordinate, neutral Mo(V) complexes containing eight sulfur atoms bound to the Mo in the Mo coordination sphere and have been prepared in non-aqueous media by reacting a substituted ammonium tetrathiomolybdate with a thiuramdisulfide in non-aqueous media under an inert atmosphere. In the compound two of the sulfur atoms are bound to the Mo as a disulfide ligand.

The compounds of this invention are an example of induced internal redox in $MoS_4^{2-}$ wherein a mononuclear Mo(V) complex is formed. Using N,N,N',N'-tetraethylthiuramdisulfide as the oxidant, the product $Mo(S_2)[S_2CN(C_2H_5)_2]_3$ was obtained. This compound is a rare example of a mononuclear Mo(V) species containing eight sulfur donor atoms. The only other Mo(V) mononuclear complexes with eight sulfur donors are the $[Mo(S_2CNR_2)_4]^+$ ions reported by Nieuwpoort in 1974. The Mo(V) compounds first reported by Nieuwpoort differ from the compounds of this invention in that they are cations and have no $S_2^{2-}$ ligand.

As set forth under SUMMARY OF THE INVENTION, the compounds of this invention have the structure:

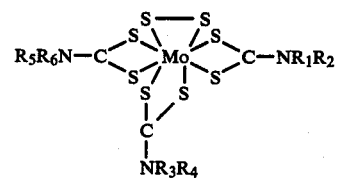

wherein $R_1$, $R_2$, $R_3$, $R_4$, $R_5$ and $R_6$ are the same or different and are H, an alkyl, aryl or cycloalkyl group. Preferably $R_1$, $R_2$, $R_3$, $R_4$, $R_5$ and $R_6$ are the same and are alkyl groups. These compounds are made by reacting one or more suitable tetrathiomolybdate salts, [Cat]$_2$MoS$_4$, wherein cat is a monovalent cation, with a thiuramdisulfide in non-aqueous media and in an inert atmosphere. Those skilled in the art know that thiuramdisulfide is the oxidized form of the dithiocarbamato ligand. The nature of the cation Cat effects both the solubility of the tetrathiomolybdate salt and the reaction rate, but does not form a part of the neutral complex products of the reaction which are the compounds of this invention. Preferably Cat will be an ammonium or substituted ammonium cation $NH_aR_{4-a}$ wherein a is 0, 1, 2, 3 or 4 and wherein R comprises an alkyl, cycloalkyl or aryl group or mixture thereof. More preferably Cat will be a tetraalkyl ammonium cation, $[NR_4]^+$.

Thiuramdisulfides useful for forming the compounds of this invention have the formula:

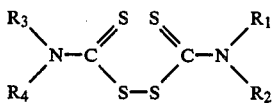

wherein $R_1$, $R_2$, $R_3$ and $R_4$ are the same or different and are H, alkyl, aryl and cycloalkyl groups. Preferably $R_1$, $R_2$, $R_3$ and $R_4$ are the same and are alkyl groups. It should be understood that if the R groups on the thiuramdisulfide are different, then one will obtain an isomeric mixture of the neutral Mo(V) complex compounds of this invention.

Dark brown crystals of $Mo(S_2)[S_2CN(C_2H_5)_2]_3$ were grown by vapor diffusion of diethylether into a $CHCl_3$ solution of the compound. A crystal was mounted on a diffractometer. Crystal data were obtained on a computer controlled Four Circle Nicolet Autodiffractometer equipped with a graphite-monochromatized MoK ($\lambda = 0.71073$ Å) radiation source. The crystal was found to be monoclinic with space group $C2/C-C_2^6h$. Least squares refinement of 15 computer centered reflections ($2\theta > 20°$) at ambient temperature of $20° \pm 1°$ C. gave the following lattice constants: $a = 16.273$ Å; $b = 11.025$ Å $c = 31.219$ Å; $\beta = 94.57°$. Its cell volume of 5584 Å$^3$ and $Z = 8$ gave a calculated density of 1.44 g/ml.

Crystal intensity measurements were made and the structure was solved to $R = 0.049$ using standard procedures.

The structural studies of the $Mo(S_2)[S_2CN(C_2H_5)_2]_3$ showed it to be eight-coordinate with six sulfur donor atoms from three dithiocarbamate ligands and two sulfur donors from a disulfide ligand. The eight sulfur atoms describe a distorted dodecahedron around the molybdenum. The bond lengths about the Mo atoms in the coordination sphere of the $Mo(S_2)[S_2CN(C_2H_5)_2]_3$ are set forth in the Table below. The S-S distance of 2.022 Å reveals the presence of the $S_2^{2-}$ ligand in this mononuclear complex.

| Bond* | Length, Å |
|---|---|
| Mo—S (dtc) | 2.534 |
| Mo—S (dtc) | 2.523 |
| Mo—S (dtc) | 2.553 |
| Mo—S (dtc) | 2.516 |
| Mo—S (dtc) | 2.496 |
| Mo—S (dtc) | 2.507 |
| Mo—S (disulfide) | 2.445 |
| Mo—S (disulfide) | 2.418 |
| S—S (disulfide) | 2.022 |

*(dtc) refers to sulfur atoms which are part of dithiocarbamate ligands.
(disulfide) refers to sulfur atoms which are part of the $S_2^{2-}$ ligand.

The invention will be further understood by reference to the following Examples.

EXAMPLES

Acetonitrile (Burdick & Jackson) was refluxed over $CaH_2$ and distilled before use. Chloroform (Fisher, reagent grade) and ether (MCB, anhydrous) were used as received. N,N,N',N'-tetraethyl thiuramdisulfide (Aldrich) was used as received. $(NH_4)_2MoS_4$ (SPEX) was also used as received. N,N,N',N'-tetraisobutyl thiuramdisulfide was prepared according to Rothstein, et al., "Note Sur La Preparatione des Tetraalkylthiurames," Recueil. Trav. Chim., 73, 561-2 (1975).

Bis(tetraethylammonium)tetrathiomolybdate(VI) $[N(C_2H_5)_4]_2MoS_4$ was prepared using the following method. All operations were carried out under $N_2$ except the work-up which was carried out in air. $(NH_4)_2MoS_4$ (25.6 g) was first ball-milled to a fine powder. $[N(C_2H_5)_4]OH$ (25% in methanol, Fluka) (150 g) was added to 250 ml methanol. This solution was added to the $(NH_4)_2MoS_4$ powder. The resulting mixture was stirred for about 18 h. The orange-red precipitate was filtered, washed with methanol, diethylether and air dried. Further drying was carried out under vacuum. The yield was 40.7 g (85%). The absence of any $NH_4^+$ in the product was confirmed by its infrared spectrum.

In the following examples all operations were conducted under an inert atmosphere such as argon.

EXAMPLE 1

Preparation of disulfidotris(N,N-diethyl dithiocarbamato)molybdenum(V)

A degassed solution containing 4.0 g (0.0135 mol) of tetraethylthiuram disulfide (Aldrich) in 30 ml of acetonitrile, was added dropwise to a degassed slurry containing 2.58 g (0.0053 mol) of bis(tetraethylammonium)-tetrathiomolybdate (TEA$_2$MoS$_4$) in 10 ml acetonitrile. The mixture was stirred under argon for two hours. 0.9 grams of the brown, solid product $Mo(S_2)[S_2CN(C_2H_5)_2]_3$, was then filtered under argon, washed with 50 ml of a diethylether/acetonitrile mixture (5/1 v/v), and recrystallized from chloroform and diethylether.

EXAMPLE 2

Preparation of disulfidotris(N,N-diisobutyldithio carbamato)molybdenum(V)

A degassed solution of 4.10 g (0.010 mol) tetraisobutylthiuram disulfide in a mixture of 15 ml $CH_2Cl_2$ and 15 ml acetonitrile was prepared and added dropwise to a slurry of 1.95 g (0.0035 mol) of bis(tetraethyl ammonium)tetrathiomolybdate (TEA$_2$MoS$_4$) in 10 ml acetonitrile. The mixture was stirred under argon at room temperature for one hour. Following the reaction, the solvent was removed by evaporation, and the resultant residue was first washed with hexane, then redissolved in acetonitrile and filtered. 1.1 grams of the brown solid product, $Mo(S_2)[S_2CN(C_4H_9)_2]_3$, was isolated from this filtrate by evaporation and recrystallized.

What is claimed is:

1. Mononuclear, eight-coordinate, neutral (disulfido)-tris(N,N-substituted dithiocarbamato)Mo(V) complexes containing only eight sulfur atoms in the Mo coordination sphere.

2. The complexes of claim 1 having the general formula $MoS_2(S_2CNR_2)_3$ wherein R is H, an alkyl group, cycloalkyl group, aryl group or mixture thereof.

3. The complexes of claim 2 wherein R consists of alkyl group.

4. Complexes of the structure

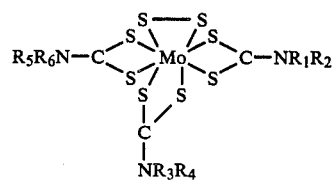

wherein $R_1$, $R_2$, $R_3$, $R_4$, $R_5$ and $R_6$ are the same or different and are H, alkyl group, cycloalkyl group, aryl group or mixture thereof.

5. The complexes of claim 4 wherein $R_1$, $R_2$, $R_3$, $R_4$, $R_5$ and $R_6$ are alkyl.

6. The complexes of claim 5 wherein $R_1$, $R_2$, $R_3$, $R_4$, $R_5$ and $R_6$ are the same.

7. A method of preparing a mononuclear, eight-coordinate, neutral (disulfido)tris(N,N substituted dithiocarbamato)Mo(V) complex containing only eight sulfur atoms in the Mo coordination sphere, said process comprising reacting, in an inert atmosphere, a tetrathiomolybdate salt of the formula $[Cat]_2MoS_4$ with a thiuramdisulfide in non-aqueous media for a time sufficient to form said complex.

8. The process of claim 7 wherein Cat is an ammonium or substituted ammonium cation.

9. The process of claim 8 wherein Cat is a tetraalkyl ammonium cation.

10. The process of either of claims 7, 8 or 9 wherein said thiuramdisulfide has the formula

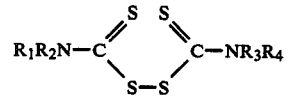

wherein $R_1$, $R_2$, $R_3$ and $R_4$ are the same or different and are H, alkyl, cycloalkyl, and aryl groups or mixture thereof.

11. The process of claim 10 wherein $R_1$, $R_2$, $R_3$ and $R_4$ are the same.

12. The process of claim 11 wherein $R_1$, $R_2$, $R_3$ and $R_4$ are the same and are alkyl.

* * * * *